United States Patent
Amor

(10) Patent No.: US 7,914,495 B2
(45) Date of Patent: Mar. 29, 2011

(54) THREE-WAY STOPCOCK

(75) Inventor: Vicente Gomez Amor, Madrid (ES)

(73) Assignee: Gobat Suministros Medicos, S.L., Madrid (ES)

( * ) Notice: Subject to any disclaimer, the term of this patent is extended or adjusted under 35 U.S.C. 154(b) by 539 days.

(21) Appl. No.: 10/582,005

(22) PCT Filed: Oct. 29, 2004

(86) PCT No.: PCT/ES2004/000477
§ 371 (c)(1),
(2), (4) Date: Feb. 2, 2007

(87) PCT Pub. No.: WO2005/046786
PCT Pub. Date: May 26, 2005

(65) Prior Publication Data
US 2008/0275399 A1 Nov. 6, 2008

(30) Foreign Application Priority Data

Dec. 11, 2003 (ES) .................. 200302597 U

(51) Int. Cl.
*A61M 5/178* (2006.01)
(52) U.S. Cl. .................................. 604/167.05
(58) Field of Classification Search ............ 604/167.05, 604/246, 256, 905, 31, 248
See application file for complete search history.

(56) References Cited

U.S. PATENT DOCUMENTS

| | | | |
|---|---|---|---|
| 3,750,704 A | 8/1973 | Burke et al. | |
| 4,219,021 A * | 8/1980 | Fink | 137/556.6 |
| 4,821,996 A | 4/1989 | Bellotti et al. | |
| 5,443,453 A | 8/1995 | Walker et al. | |
| 6,626,884 B1 | 9/2003 | Dillon et al. | |
| 7,033,339 B1 * | 4/2006 | Lynn | 604/256 |

FOREIGN PATENT DOCUMENTS

| | | |
|---|---|---|
| ES | 1052679 | 1/2003 |
| WO | 8806895 | 9/1988 |
| WO | 03082396 | 10/2003 |

OTHER PUBLICATIONS

International Search Report for related PCT Application No. PCT/ES2004/000477.

* cited by examiner

*Primary Examiner* — Nicholas D Lucchesi
*Assistant Examiner* — Brooke M Matney
(74) *Attorney, Agent, or Firm* — McDermott Will & Emery, LLP

(57) ABSTRACT

A 3-way stopcock for medical use is described and includes a body or nucleus (1) wherein a principal arm (2) and two secondary arms (3, 3') converge and a plug or stopper (4) acting inside the body or nucleus (1). According to the invention, the two secondary arms (3, 3') present initial curved flexible segments (3a, 3'a) having a high elastic index, which respectively extend into parallel final distal segments (3b, 3'b).

3 Claims, 1 Drawing Sheet

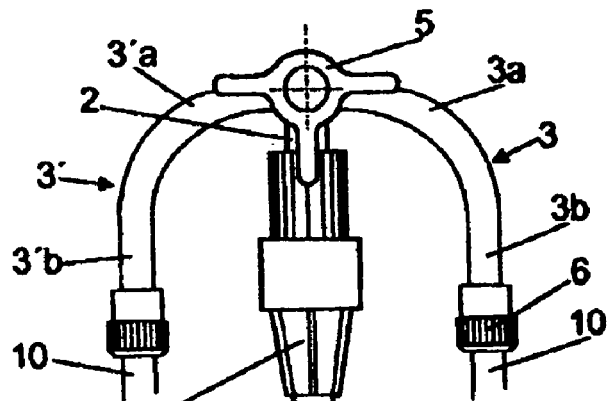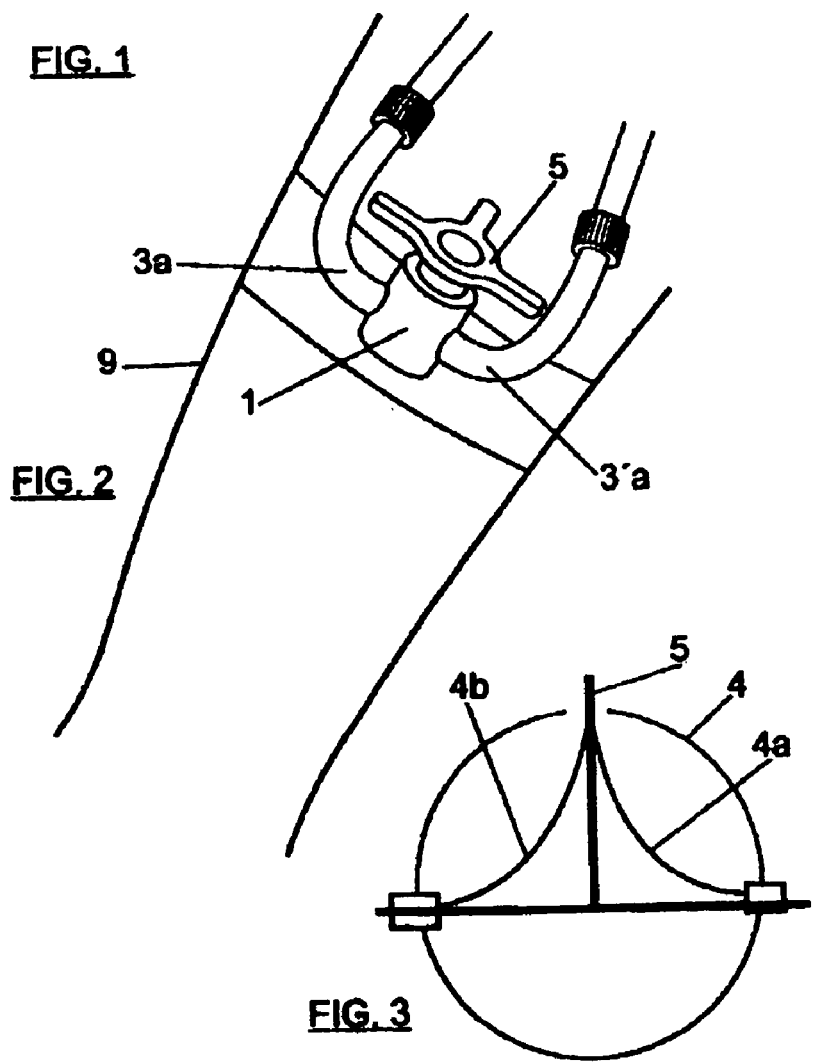

THREE-WAY STOPCOCK

FIELD AND OBJECT OF THE INVENTION

The present invention is a 3-way stopcock, useful in the medical field, in which arms or channels attach to an intravenous catheter or needle while other arms are used for administration of intravenous fluids.

The object of the invention is to achieve an optimal functioning 3-way stopcock, obtaining an improvement in the way the arms or channels relate to intravenous bottles or containers, which hold therapeutic products. Another objective is to attain greater adaptability of the stopcock to the needs of the patient.

BACKGROUND OF THE INVENTION

3-Way stopcocks are widely used in the medical and sanitary field for the administration of different products, such as serum, nutrients and medications through an intravenous catheter. Patients with dementia, other co-existing pathologies and cardiovascular problems are those that need most this type of stopcock for simultaneous infusion of one or more intravenous medications.

Spanish utility patent U 2002 02098 (ES-U-1 052 679) describes a 3-way stopcock that is characterized by two secondary arms or routes that emerge from a nucleus forming orthogonal elbows in its trajectory.

As medications and nutrients administered to patients intravenously are solutions consisting fundamentally of solid micro-elements in liquid state, the micro-elements can become deposited on the walls of the arms or channels thus impairing adequate flow of liquids. Therefore, the presence of orthogonal elbows in the stopcock described in the previously-mentioned patent can present the difficult to eliminate problem of occlusion of the arms or channels. This problem has negative consequences on intravenous therapy because the medication that goes to the patient needs to be administered in a specific period of time.

Another problem presented by the previously described stopcock having orthogonal elbows is reduced flexibility. For example, for the situation where medical personnel need to manipulate the arms or channels, e.g., during changing of intravenous containers or bottles containing intravenous therapy products or to disconnect a secondary line from the main catheter, damage can occur to the principal arm connection with the intravenous catheter, thus affecting the supplying of these products. Because the principal arm is directly connected to the catheter inserted previously in the patient's vein, any manipulation on the secondary arms will significantly affect the intravenous connection, producing pressure leaks. Therefore, in view of this problem, it would be desirable to have a 3-way stopcock in which the secondary arms are flexible.

DESCRIPTION OF THE INVENTION

In view of the previously outlined, obstruction problems in the secondary arms or channels and reduced flexibility of these, an improved 3-way stopcock has been developed so as to resolve and satisfy these problems. In addition, thanks to this new designed configuration, the stopcock in this invention provides greater flexibility. Therefore, sanitary personnel can handle the secondary arms with greater ease and safety. In the event of acting on secondary arms or routes this will not affect the principal arm or channel. In this way, the secondary arms or routes can be moved with a greater degree of liberty and therefore, intravenous therapy results in no damage for the patient. This way, a problem such as pressure leakage is solved by the present invention.

The 3-way stopcock for sanitary use developed by the present invention, solves obstruction problems cited before, on the bases of eliminating the orthogonal trajectories of the secondary arms, substituting them for curved trajectories.

According to the first objective of this invention, the 3-way stopcock, that is of those that consists of a cylindrical nucleus or body that has inside a plug or stopper worked by a handle, in which said nucleus converge a principal arm connected to a catheter introduced in the patient's vein and two secondary arms or channels that receive other catheters that supply medications or therapeutic fluids, these two secondary arms are diametrically opposite, out of phase orthogonally with respect to the principal arm, because these secondary arms are characterized by an initial curvature, flexible and with a high elastic index which later continue in their final portions sensibly parallel to each other.

Thus, so much as the intravenous catheter, as also the two connection catheters of the secondary arms of the stopcock run sensibly in parallel and are oriented towards the head of the bed of the patient who is receiving intravenous therapy. This is the most favourable direction since the bottles or containers that contain medications or nutrients are usually at the head of the patient.

The curvatures and flexibility of the initial portion of the secondary arms permit that the secondary arms do not present obstructions, whereupon, intravenous therapy presents a greater efficacy because the volume of medication and nutrients to be infused is carried out in the required time. In addition, the initial portions present a high index of elasticity so as the capacity to return to its initial position is greater, permitting the secondary arms to be used with greater degree of safety.

Accordingly fulfilling of the invention, the plug or stopper situated in the cavity of the nucleus or body has an interior configuration sensibly in form of an inverted "V" to permit therapeutic fluids to pass simultaneously and at the same time, permit flow of fluid to one of the secondary arms, closing off the flow to the other and even, close the flow to both secondary arms if needed.

Accordingly, another fulfilment of this invention, the principal and secondary arms will be made of medical grade polymers or plastic.

BRIEF DESCRIPTION OF DRAWINGS

While certain embodiments/aspects of the present disclosure are described herein, other embodiments/aspects according to the present disclosure will become readily apparent to those skilled in the art from the following detailed description, wherein exemplary embodiments are shown and described by way of illustration. In the drawings:

FIG. 1: represents perspective view of a perfected 3-way stopcock for sanitary application according to the present invention.

FIG. 2: Represents the 3-way stopcock place for use and properly implanted in the patient's foreman according to the present invention.

FIG. 3: Represents plug or stopper of the stopcock according to the present invention.

DETAILED DESCRIPTION OF EMBODIMENT OF THE INVENTION

With reference to FIGS. 1-3, it can be observed how the 3-way stopcock consists of a cylindrical body or nucleus (1)

in which the plug or stopper (4) works and where the principal arm or channel (2) and its two secondary arms (3,3') meet or converge. Between these three arms they communicate or not depending on the position that the plug (4) adopts, which is operated by health care workers via the handle (5). As stated before, the principal arm (2) is assigned to receive an intravenous catheter (11) placed in the patient, while the secondary arms or channels (3, 3') are assigned to receive other catheters or lines (10,10'), whereupon relating the stopcock of the invention with some containers supplying therapeutic fluids, for example: saline solution, antibiotics or any other equal products.

According to the present invention, the secondary arms (3, 3') that emerge from the body or nucleus (1) in diametric opposition is each configured such that an initial segment is curved (3a, 3a') and a final segment of each (3b,3b') runs parallel to the principal arm (2). The direction of inclination of the curved segments is toward the patient's shoulder. This way. it prevents the problem of occlusion or blocking of the secondary arms.

The means for coupling (6) that is used for connecting the 3-way stopcock to the corresponding catheters can be by universal connectors or luer-lock, which are used in medical practice.

When the 3-way stopcock is connected to the intravenous catheter properly placed in the patient's forearm (9) according to FIG. 2, the secondary arms (3, 3') present curved. segments (3a, 3a') which avoid accumulation of solids and therefore eliminate the risk of occlusion of its channels.

By means of the distal segments (3b, 3b') which arc the prolongation of the curved segments (3a, 3a') and the catheters (10,10') remain visibly parallel between themselves and are oriented longitudinally along the forearm heading towards the patient's shoulder, that is, in the most ideal position for the catheters (10, 10') connected to the distal segments (3b, 3b') of the secondary arms communicate with the corresponding containers or bottles supplying therapeutic fluids. These bottles usually hang from a support in the form of a "T" placed at the head of the bed. Therefore, in the position in which the stopcock acts, according to the present invention, it turns out to be impossible for said catheters (10, 10') to choke off or kink, thus making difficult or impeding the flow of therapeutic fluids. In addition, the stopcock of the present invention provides for, the non-occlusion of the arms due to the curved portions or segments (3a, 3a').

The 3-way stopcock present invention is made out of medical grade polymer, this is a polymer resistant to thermal treatment received in sterilization. It does not interact with therapeutic fluids and has to be easy to manipulate, etc. In addition, the initial portions (3, 3') have a high elastic index, which produces a greater capacity to return to its original position. This provides a stopcock offering greater security for the patient and a higher capacity for manipulation on the part of sanitary personnel.

FIG. 3 shows the interior of stopper or plug (4), in which the configuration of the inner channels (4a, 4b) is in the form of an inverted "V," having its branches slightly arched so as to permit optimal flow of fluids.

The invention claimed is:

1. A three-way stopcock for medical use comprising:
    a primary arm and two secondary arms meeting at and integral with a body, wherein the primary and secondary arms are configured and arranged to receive an intravenous catheter and two supply catheters, respectively; and
    a plug disposed within the body, wherein the plug is configured and arranged for being externally activated by a handle;
    wherein the principle arm and the secondary arms can be brought to selectively communicate with each other or be disconnected, and wherein the two secondary arms protrude diametrically opposite from the body, wherein the tangent of both arms nearest the body is perpendicular to the principal arm, wherein each secondary arm has (i) a proximal segment adjacent to the body that is curved and flexible, and (ii) a distal segment integral with the respective proximal segment and having an end with means for coupling to a corresponding catheter, wherein the two distal segments can be configured essentially parallel to each other and the primary arm, wherein the two proximal segments can be oriented in a direction perpendicular to the principal arm.

2. The three-way stopcock according to claim 1, wherein the secondary arms are made of medical grade polymer.

3. The three-way stopcock according to claim 1, wherein the plug presents in its interior inner channels an interior configuration in the form of inverted "V", wherein the branches are slightly arched.

* * * * *